United States Patent
Schmit Deroin

(10) Patent No.: US 12,408,690 B2
(45) Date of Patent: Sep. 9, 2025

(54) VEGETABLE WATER

(71) Applicant: Fabrice Thueler, Delémont (CH)

(72) Inventor: Camille Schmit Deroin, Chernex (CH)

(73) Assignee: Fabrice Thueler, Delémont (CH)

( * ) Notice: Subject to any disclaimer, the term of this patent is extended or adjusted under 35 U.S.C. 154(b) by 704 days.

(21) Appl. No.: 17/442,151

(22) PCT Filed: Feb. 11, 2020

(86) PCT No.: PCT/IB2020/051064
§ 371 (c)(1),
(2) Date: Sep. 23, 2021

(87) PCT Pub. No.: WO2020/165747
PCT Pub. Date: Aug. 20, 2020

(65) Prior Publication Data
US 2022/0167651 A1    Jun. 2, 2022

(30) Foreign Application Priority Data

Feb. 12, 2019 (CH) .................................. 0169/19

(51) Int. Cl.
| | | |
|---|---|---|
| *A23L 33/105* | (2016.01) | |
| *A23G 9/42* | (2006.01) | |
| *A23L 2/02* | (2006.01) | |
| *A23L 19/00* | (2016.01) | |
| *A61K 8/9789* | (2017.01) | |
| *A61K 36/28* | (2006.01) | |
| *A61K 36/87* | (2006.01) | |
| *C12G 3/00* | (2019.01) | |

(52) U.S. Cl.
CPC .............. *A23L 33/105* (2016.08); *A23G 9/42* (2013.01); *A23L 2/02* (2013.01); *A23L 19/00* (2016.08); *A61K 8/9789* (2017.08); *A61K 36/28* (2013.01); *A61K 36/87* (2013.01); *C12G 3/00* (2013.01); *A23V 2002/00* (2013.01)

(58) Field of Classification Search
CPC ..... A23L 33/105; A23L 19/00; A61K 8/9789; A61K 2/02; A61K 36/28; A61K 36/87; A23G 9/42; C12G 3/00; A23V 2002/10
See application file for complete search history.

(56) References Cited

U.S. PATENT DOCUMENTS

2018/0092382 A1*  4/2018  van Manen ............... A23L 2/56

FOREIGN PATENT DOCUMENTS

| | | |
|---|---|---|
| ES | 2393901 | 12/2012 |
| JP | 2001252054 | 9/2001 |
| JP | 2019033758 | * 3/2019 |
| KR | 101445776 | * 10/2014 |
| WO | WO 9419967 | 9/1994 |
| WO | WO 0004794 | 2/2000 |
| WO | WO 2005046358 | 5/2005 |
| WO | WO 2011085429 | 7/2011 |

OTHER PUBLICATIONS

Laqua Horiba (Rev 1.0 Apr. 2016).*
Kannangara et al. (j. Pharmacognosy and Phytochemistry.*

* cited by examiner

*Primary Examiner* — Shirley V Gembeh
(74) *Attorney, Agent, or Firm* — Studebaker Brackett PLLC

(57) ABSTRACT

The invention relates to a plant-based water extracted from plants such as a fruit and/or a vegetable and/or a plant, the water containing a total concentration of dissolved substances in the plant-based water, in an amount up to 15 mg/l, the water having a pH of from 4 to 7, an rH2 that is neutral or close to neutral and a very low conductivity of less than 50 uS/cm.

14 Claims, No Drawings

VEGETABLE WATER

The present invention relates to a water derived from plant materials by a natural physical process, notably a water extracted by drying, without chemical solvents and to the use thereof notably in food compositions, drinks and healthcare.

The dehydration of plants, without recovering and reusing the plant-based water, is a process that has been carried out by numerous civilisations for years as is described in the following Internet links: https://www.deshydrateur.biz, and http://www.ronalpenford.com/pouvez-vous-deshydrater-les-aliments-utilisation-du-soleil/. Furthermore, it is one of the oldest methods of preserving food.

Nowadays, consumers are increasingly concerned about their health and are mindful of the origin and nature of the foods that they consume.

Water is an element that is essential to life. It is used to provide the body with vitality, but also to hydrate it so that it can carry out its daily functions.

Today, the water sold by the authorities or agri-food companies is terrestrial water whereas the plant-based water of this invention is itself derived from the plant kingdom.

The waters originating from the plant kingdom today are obtained either by mechanical pressure, which constitute juices in the form of plant concentrates to which terrestrial water is added, or by distillation, or even by other processes.

For the well-being of the body, it is ideally necessary to absorb a pure living water that is compatible with human physiology. This is not so easy today, both municipal water and PET-bottled water have shortcomings regarding these points, notably by containing numerous residues of medications and agricultural pesticides.

Water carries out a transportation function in our body, and not a supply function. The role of water is rather to assist the metabolism by transporting nutritional substances to the cells and by clearing the body of toxic metabolic waste, such as uric acid.

The objective of the present invention is to provide a water derived from plant materials that is free of limestone and low in salts and in organic and mineral substances and which ideally supports the functions of the metabolism.

Another objective of the present invention is to recover and reuse this plant-based water without deteriorating it in order to supply the animal kingdom.

The plant-based water of the present invention is recovered by a gentle extraction from the plants which makes it possible not to deteriorate said plant-based water so that it can be consumed by the animal kingdom notably in the form of a drink, food, medication, food supplement or cosmetic. The plant-based water of the present invention therefore makes it possible to feed, hydrate and enhance the animal world.

Owing to a gentle evaporation of the water present in the fruit, vegetable or plant, only the $H_2O$ molecules derived from the plants are recovered whilst the organic matter, with the enzymes, vitamins and mineral salts remain in the plants.

Plant-based water is an unusual type of water. Plant-based water is composed of $H_2O$ molecules contained in the plant kingdom, circulating in the plants, notably fruits, vegetables or plants.

In accordance with the invention, the water extracted from plants, such as a fruit and/or a vegetable and/or a plant, contains a total concentration of substances dissolved in the plant-based water, in an amount of between 1 and 7 mg/l, the water has a pH of from 4 to 7, an rH2 that is neutral, 28, or close to neutral, typically from 25 to 30, and a very low conductivity of less than 50 uS/cm, or less than 25 uS/cm, or even less than 10 uS/cm.

Preferably, the plant-based water is extracted by drying fruits, vegetables or plants.

Preferably, the plant-based water contains solids dissolved in the water in an amount of less than 10 mg/l.

In another embodiment, the composition further comprises additional adjuvants.

In one embodiment, the plant-based water is used in the cosmetic field, for example as makeup-remover lotion.

In another embodiment, the plant-based water is used in the medical field, notably for treating cancer, rheumatism, gout, chronic infections, cellulite.

In another embodiment, the plant-based water is placed in a packaging such as a bottle or carton, as a drink or food supplement.

In another embodiment, the plant-based water may be composed of an assortment of fruits and/or vegetables and/or plants, optionally dried at the same time in a dedicated machine.

Various extraction techniques exist in order to obtain this plant-based water, which are carried out while taking care to keep aside all the nutrients and vitamins contained in each of the cells of these plants. Thus, it is therefore possible to obtain the plant-based water notably by distillation or evaporation.

For example, in the context of distillation, it would be suitable to press plants in order to obtain a concentrated liquid and to carry out the extraction of the plant-based water at low pressure with a combination of a high stirring speed and an ultra rapid increase in temperature. The heat contact time does not exceed a few seconds, thus preserving the delicate constituents entrained by the vapor.

In the context of evaporation, it is advisable to carry out a gentle dehydration of the plants performed at low temperature and low pressure in order to enable the evaporation of the water of constitution of these plants. Directly collected at the heart of the plants, the plant-based water extracted retains all the essential elements.

Low-temperature drying enables a virtually complete extraction of the water contained in the plants. Specifically, it is advisable to carry out a gentle dehydration, by low-temperature drying of the plants carried out at low temperature, a temperature below 60° C., and low pressure in order to enable a gas supply in the form of hot air which gives rise to an evaporation of the water contained in the plants. Directly collected at the heart of the plants, the plant-based water extracted is pure. It does not contain calories but may contain a few tiny traces of organic substances (lipids, carbohydrates and proteins).

Another advantage of the present invention is that, on the one hand, a pure plant-based water is recovered that contains virtually only $H_2O$ molecules and that, on the other hand, the dry plant material is ready to be consumed or to be used for various preparations.

In one embodiment, the plant-based water is used as a food product or as an alcoholic or non-alcoholic drink.

According to this embodiment, the plant-based water is used for the preparation of beer for example.

Still according to this embodiment, the plant-based water is used for the preparation of a sorbet or an ice cream for example.

No solvent is used to produce the plant-based water. Furthermore, in an ecological approach, in addition to consuming only very little energy for the extraction of the water, surplus plants or damaged plants, for example organic fruit and vegetables, can be used to extract the water therefrom.

The features of the invention will become more clearly apparent on reading this embodiment, given purely by way of example, no limitation being implied.

In this example, analysis by a laboratory has shown that an organic apple and edelweiss water has a pH of 5.1, a conductivity of 4, a total concentration of dissolved substances in the plant-based water of 2.56 ppm, and a solids concentration of less than 0.10 mg/l. In this example, the rH2 is 28.

From an organolepticpoint of view, the plant-based water obtained and characterized in the table is clear, has a very slight odor, and a mild and subtle pleasant taste. Through good prior selection, this plant-based water does not comprise uranium, arsenic, heavy metals or pesticide metabolites.

The plant-based water obtained has a pH of 5.1 in this example. The pH level reflects the acidity of the water. The pH (hydrogen potential) refers to the amount of hydrogen in the water. Drinking water that is too basic over time upsets the digestion potential of the stomach, which digestion takes place in a highly acidic medium. Thus, the continuation of the digestion does not take place properly. It is therefore advisable to drink fairly acidic, such as the water of the sample.

In one embodiment comprising a mixture of lavender and rose and *Aloe vera*, the plant-based water is used as a makeup-remover lotion. It gently cleanses and soothes. The plant-based water is an effective makeup remover owing to its active agents of plant origin and it is suitable for the most sensitive skins.

In a given example, the plant-based water may be obtained from a mixture of apples and edelweiss.

In another example that is not described, the plant-based water is derived from grapes after harvesting for the production of a plant-based water additional to the wine. The remainder of the $H_2O$ molecules contained in the grape used for the production of wine is extracted by drying in order to obtain a plant-based water. «complémentaire» à la fabrication du yin.

In order to be eco-friendly, mobile units for production of plant-based water are as close as possible to the plants.

The invention claimed is:

1. A plant-based water extracted from plants such as a fruit and/or a vegetable and/or a plant, the water containing a total concentration of dissolved substances, or Total Dissolved Solids, in the plant-based water, in an amount of between 1 mg/l and 7 mg/l, the water having a pH of from 4 to 7, a relative Hydrogen score that is neutral or close to neutral and a low conductivity of less than 50 μS/cm.

2. The plant-based water as claimed in claim 1, extracted from fruits.

3. The plant-based water as claimed in claim 1, extracted from vegetables.

4. The plant-based water as claimed in claim 1, extracted from plants.

5. The plant-based water as claimed in claim 1, extracted from edelweiss and at least one other plant.

6. The plant-based water as claimed in claim 1, the conductivity of which is less than 10 μS/cm.

7. The plant-based water as claimed in claim 1, further comprising additional adjuvants.

8. The plant-based water as claimed in claim 1, used as a cosmetic ingredient.

9. The plant-based water as claimed in claim 1, for the use thereof in the medical field, notably for treating cancer, rheumatism, gout, chronic infections, cellulite.

10. The plant-based water as claimed in claim 1, in a packaging such as a bottle or carton, as a drink or food supplement.

11. The plant-based water as claimed in claim 1, for the use thereof as a food product or as an alcoholic or non-alcoholic drink.

12. The plant-based water as claimed in claim 11, used for the preparation of beer, whiskey or any other spirits.

13. The plant-based water as claimed in claim 11, used for the preparation of a sorbet or an ice cream.

14. The plant-based water as claimed in claim 1, extracted from pressed grapes after the production of wine.

* * * * *